US 6,956,156 B2
Oct. 18, 2005

(54) INBRED SUNFLOWER LINE H1063R

(75) Inventors: James T. Gerdes, Breckenridge, MN (US); Joseph J. Caroline, Breckenridge, MN (US)

(73) Assignee: Agrigenetics, Inc., Indianapolis, IN (US)

( * ) Notice: Subject to any disclaimer, the term of this patent is extended or adjusted under 35 U.S.C. 154(b) by 0 days.

(21) Appl. No.: 10/809,771

(22) Filed: Mar. 25, 2004

(65) Prior Publication Data

US 2004/0187180 A1 Sep. 23, 2004

Related U.S. Application Data

(62) Division of application No. 10/122,422, filed on Apr. 16, 2002.
(51) Int. Cl.$^7$ ............................ A01H 5/00; A01H 5/10; A01H 1/00; A01H 1/02; C12N 5/04
(52) U.S. Cl. ...................... 800/322; 800/264; 800/268; 800/269; 800/274; 800/278; 800/279; 800/288; 800/300; 800/302; 800/303; 435/416; 435/421; 435/428; 435/430; 435/430.1
(58) Field of Search ................................. 800/264, 268, 800/269, 274, 278, 279, 288, 300, 302, 303, 322; 435/416, 421, 428, 430, 430.1

(56) References Cited

U.S. PATENT DOCUMENTS

| 5,523,520 A | * | 6/1996 | Hunsperger et al. | ........ 800/260 |
| 5,866,766 A | * | 2/1999 | Cole | ........................ 800/260 |
| 6,069,304 A | * | 5/2000 | Cole | ........................ 800/322 |

OTHER PUBLICATIONS

Perez–Vich et al. Theor Appl Genet 100: 105–111 (2000).*
Kraft et al. Theor Appl Genet 101: 323–326 (2000).*
Eshed et al. Genetics 143: 1807–1817 (1996).*
Young et al. Theor Appl Genet 77: 353–359 (1989).*
Zeven et al. Euphytica 32: 319–327 (1983).*

* cited by examiner

Primary Examiner—David T. Fox
Assistant Examiner—Keith O. Robinson
(74) Attorney, Agent, or Firm—Kenneth Ludwig

(57) ABSTRACT

An inbred sunflower line, designated H1063R, is disclosed. The invention relates to the seeds of inbred sunflower line H1063R, to the plants of inbred sunflower line H1063R and to methods for producing a sunflower plant, either inbred or hybrid, by crossing the inbred line H1063R with itself or another sunflower line. The invention further relates to methods for producing a sunflower plant containing in its genetic material one or more transgenes and to the transgenic plants produced by that method and to methods for producing other inbred sunflower lines derived from the inbred H1063R.

25 Claims, No Drawings

INBRED SUNFLOWER LINE H1063R

CROSS REFERENCE

This application is a divisional of U.S. patent application Ser. No. 10/122,422 filed Apr. 16, 2002.

BACKGROUND OF THE INVENTION

The present invention relates to a new and distinctive sunflower inbred line, designated H1063R. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include improved seed yield, earlier maturity, shorter plant height, uniformity of plant type and disease and insect resistance. High oil percentage is important in breeding oilseed types whereas large seed size, a high kernel-to-hull ratio, and uniformity in seed size, shape, and color are important objectives in breeding and selection of nonoilseed sunflower. Other characteristics such as improved oil quality are also important breeding objectives.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Sunflower (*Helianthus annuus* L.), can be bred by both self-pollination and cross-pollination techniques. The sunflower head (inflorescence) usually is composed of about 1,000 to 2,000 individual disk flowers joined to a common base (receptacle). The flowers around the circumference are ligulate ray flowers with neither stamens nor pistil. The remaining flowers are hermaphroditic and protandrous disk flowers.

Natural pollination of sunflower occurs when flowering starts with the appearance of a tube partly exerted from the sympetalous corolla. The tube is formed by the five syngenesious anthers, and pollen is released on the inner surface of the tube. The style lengthens rapidly and forces the stigma through the tube. The two lobes of the stigma open outward and are receptive to pollen but out of reach of their own pollen initially. Although this largely prevents self-pollination of individual flowers, flowers are exposed to pollen from other flowers on the same head by insects, wind and gravity.

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 generations from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior sunflower inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same sunflower traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new sunflower inbred line.

The development of commercial sunflower hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

A reliable method of controlling male fertility in plants offers the opportunity for improved plant breeding. This is especially true for development of sunflower hybrids, which relies upon some sort of male sterility system. Two types of male sterility, genetic and cytoplasmic, have been found in sunflower.

Hybrid sunflower seed is typically produced by a male sterility system incorporating genetic or cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in sunflower plants, since only the female provides cytoplasm to the fertilized seed. CMS plants are fertilized with pollen from another inbred that is not male-sterile. Pollen from the second inbred may or may not contribute genes that make the hybrid plants male-fertile.

Hybrid sunflower seed is typically produced by a male sterility (CMS) system. Alternate strips of two sunflower inbreds, male and female, are planted in a field. Providing that there is sufficient isolation from sources of foreign sunflower pollen, florets of the female (CMS) inbred will be fertilized only from the other inbred (male). Pollen is typically transferred by bees placed in the field and the resulting seed is therefore hybrid and will form hybrid plants.

Plant breeding methods involving genetic or cytoplasmic male sterility, or induction of male sterility by gibberellic acid, allow for complete hybridization of lines and hence greater precision in estimating combining ability. Various tester parents and tester schemes are being used. A. V. Anaschenko has conducted extensive testing for general combining ability by the top cross method with chemical emasculation of the female parent with gibberellic acid. He has used open pollinated cultivars, hybrids and inbred lines as testers. A. V. Anaschenko, The Initial Material for Sunflower Heterosis Breeding, Proceedings of the 6th International Sunflower Conference, 391–393 (1974). V. Vranceanu used a monogenic male sterile line as a female parent to test for general combining ability and subsequent diallel cross analysis with artificial emasculation to test for specific combining ability. V. Vranceanu, Advances in Sunflower Breeding in Romania, Poc. 4th International Sunflower Conference (Memphis, Tenn.), 136–146 (1970). Recent testing by breeders in the United States has included the rapid conversion of lines to cytoplasmic male sterility by using greenhouses and winter nurseries and subsequent hybrid seed production in isolated crossing blocks using inbred lines as tester.

There are several methods of conferring genetic male sterility available, such as multiple mutant genes at separate locations within the genome that confer male sterility. According to A. I. Gundaev, Prospects of Selection in Sunflower for Heterosis, Sb. Rab. Maslichn. Kult., 3:15–21 (1966), genetic male sterility first was reported in the Soviet Union by Kuptsov in 1934. Since then, numerous investigators have reported genetic male sterility in sunflower. Vranceanu indicated isolation of more than thirty sources of male sterility in the Romanian program, most of which were controlled by a single recessive gene. Diallel cross analysis of ten of these lines indicated the presence of five different genes. The studies of E. D. Putt and C. B. Heise, Jr. were some of the first reported to assess the value of genetic male sterility to produce hybrid seed. They concluded that the lines of partial male sterility may have the most immediate value in commercial production of hybrid seed as not only could the partial male sterile lines hybridize well in crossing plots, they could also be increased and easily maintained. E. D. Putt and C. B. Heiser, Jr., Male Sterility and Partial Male Sterility in Sunflowers, Crop Science, 6:165–168 (1966).

In order to produce hybrid seed using complete genetic male sterility, the male sterile locus must be maintained in the heterozygous condition in the female parent. This is accomplished by sib pollinations of male sterile plants (ms ms) with heterozygous male fertile plants (Ms ms) within the female parent. The resultant progeny from the male sterile plants will segregate 1:1 for fertile and sterile plants. When such lines are used in hybrid seed production the fertile plants must be removed prior to flowering to obtain 100% hybridization with the male parent line.

The laborious, and occasionally unreliable, genetic male sterility system can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in sunflower plants, since only the female provides cytoplasm to the fertilized seed. CMS plants are fertilized with pollen from another inbred that is not male-sterile. Pollen from the second inbred may or may not contribute genes that make the hybrid plants male-fertile.

Cytoplasmic male sterile lines are traditionally developed by the backcrossing method in which desirable lines that have undergone inbreeding and selection for several generations are crossed initially to a plant with cytoplasmic male sterility. Thereafter the inbred line to be converted is used as a recurrent parent in the backcrossing procedure. The final progeny will be genetically similar to the recurrent parent except that it will be male sterile.

Fertility restorer lines are developed by transferring a dominant restorer gene to an established inbred line with normal cytoplasm by backcrossing. If this procedure is used, selected plants must be crossed to a cytoplasmic male sterile line after each generation to determine if the fertility restorer genes are present. A more common procedure is self-pollination and selection of male fertile plants from commercial hybrids or planned crosses of parents having restorer genes in male sterile cytoplasm. This procedure does not require test crossing to a male sterile line during selection because the plants will be fully male fertile if the necessary restoring genes are present.

Typically most fertility-restorer lines in use today have restorer genes in male sterile cytoplasm, are resistant to older races of downy mildew and have recessive branching. The later trait extends the period of pollen production and is useful in obtaining simultaneous flowering with female lines in hybrid seed production fields. Restorer lines RHA271, RHA273, and RHA274 were the first such lines to be developed and have been used widely in producing hybrids in breeding programs throughout the world.

Other methods for conferring male sterility are also available and could be used in developing male sterile and fertility restoring sunflowers. For example, Albertsen et al., of Pioneer Hi-Bred, have developed a system of nuclear male sterility in corn which could also be used in sunflower which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

There are many other methods of conferring male sterility in the art of the plant breeding and any method can be used, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al., EPO 89/3010153.8 publication No. 329,308 and PCT application PCT/CA90/000037 published as WO 90/08828).

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see, Fabinjanski, et al. EPO 89/3010153.8 publication no. 329, 308 and PCT application PCT/CA90/00037 published as WO 90/08828).

Another version useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, G. R., U.S. Pat. No. 4,936,904). Application of the gametocide, timing of the application and genotype specifically often limit the usefulness of the approach.

Sunflower is an important and valuable field crop. Thus, a continuing goal of plant breeders is to develop stable, high yielding sunflower hybrids that are agronomically sound. The reasons for this goal are obviously to maximize the amount of grain produced on the land used and to supply food for both animals and humans. To accomplish this goal, the sunflower breeder must select and develop sunflower plants that have the traits that result in superior parental lines for producing hybrids.

SUMMARY OF THE INVENTION

According to the invention, there is provided a novel inbred sunflower line, designated H1063R. This invention thus relates to the seeds of inbred sunflower line H1063R, to the plants of inbred sunflower line H1063R and to methods for producing a sunflower plant produced by crossing the inbred line H1063R with itself or another sunflower line, and to methods for producing a sunflower plant containing in its genetic material one or more transgenes and to the transgenic sunflower plants produced by that method. This invention also relates to methods for producing other inbred sunflower lines derived from inbred sunflower line H1063R and to the inbred sunflower lines derived by the use of those methods. This invention further relates to hybrid sunflower seeds and plants produced by crossing the inbred line H1063R with another sunflower line.

The inbred sunflower plant of the invention may further comprise, or have, a cytoplasmic factor that is capable of conferring male sterility. Parts of the sunflower plant of the present invention are also provided, such as e.g., pollen obtained from an inbred plant and an ovule of the inbred plant.

In another aspect, the present invention provides regenerable cells for use in tissue culture or inbred sunflower plant H1063R. The tissue culture will preferably be capable of regenerating plants having the physiological and morphological characteristics of the foregoing inbred sunflower plant, and regenerating plants having substantially the same genotype as the foregoing inbred sunflower plant.

Preferably, the regenerable cells in such tissue cultures will be embryos, pollen, ovules, leaves, stems, cortex, pith, involucral bracts, ray flowers, disk flowers, pappi, achenes, nectaries, interfloral bracts, receptacle, trichomes stigma, anther, style, filament, calyx, pericarp, seed coat, endosperm, embryo, roots, root tips, seeds and the like. Still further, the present invention provides sunflower plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Days to Flower (FLR). Number of days from planting to beginning of flowering at Stage R5.1.

Plant height (HT). Height in inches from the ground to the point on the stem where the receptacle is attached.

Test Weight (TW). Pounds per bushel at 10% moisture basis.

Moisture (MST). Percent of seed moisture at harvest.

Percent Oleic Acid (OIL). Percent oil of the seed that is oleic acid.

Percent Oil (OIL). Percent oil of the seed adjusted to 10% moisture.

Total Saturated (TOTSAT). Total percent oil of the seed of the saturated fats in the oil including C12:0, C14:0, C16:0, C18:0, C20:0, C22:0 and C24:0.

Stage R5.1. Stage R5.1 is the stage when the ray flowers are visible and the first ring of disk flowers has emerged and flowered.

Restorer Line. A line possessing the gene or genes to restore male fertility or viable pollen to a sunflower hybrid or inbred line and progeny having a maternal cytoplasm that conditions male sterility.

Cytoplasmic Male Sterile (CMS) Plant or Inbred Line. A sunflower line that produces no viable pollen is called male sterile. Male sterility is inherited maternally, i.e., the male sterile plant is used as the female parent in a cross with pollen from another sunflower. CMS lines are produced by crossing a maintainer line with a sunflower plant with the cytoplasmic male sterility trait and then backcrossing to the maintainer line until a male sterile line that is homologous to the maintainer line in all other respects is developed. CMS lines are also referred to as female lines.

Allele. The allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

DETAILED DESCRIPTION OF THE INVENTION

Seed from sunflower line H1063R has been deposited with the American Type Culture Collection, 12301 Parklaw Drive, Rockville, MD, USA 20852 and bearing ATCC Accession Number PTA-6657. Inbred sunflower line H1063R is an oil type sunflower male line with superior characteristics, and provides an excellent parental line in crosses for producing first generation ($F_1$) hybrid sunflower.

Inbred sunflower line H1063R has the following morphologic and other characteristics (based primarily on data collected at Breckenridge, Minn.).

TABLE 1

VARIETY DESCRIPTION INFORMATION

TYPE: Oilseed
REGION WHERE DEVELOPED: Sunflower growing regions of the U.S.
COMPARISON VARIETY: RHA345
MATURITY:

Days to Stage R5.1 (from emergence): 58–3 days later than comparison
Days to physiological maturity (from emergence): 93–5 days later than comparison
PLANT:

Plant Height (at harvest ripeness): 134 cm–38 cm shorter than comparison
Stem - length of internode at harvest ripeness - 10 cm–4 cm longer than comparison
Number of leaves - 19–5 leaves fewer than comparison
Branching - Fully branched
Color of growing point: Green
LEAVES (Midstem at flowering):

Blade length - 20.0 cm–2 cm shorter than comparison
Blade width - 19.0 cm
3 cm narrower than comparison
Width: Length ratio: Narrower than long
Leaf shape: Lanceolate
Leaf apex: Acuminate
Leaf base: Auriculate
Leaf margin: Medium serrate
Depth of margin indentations: Shallow
Attitude: Ascending
Surface: Crinkled (ridged)
Color: Green
Margin Color: Green
HEAD AT FLOWERING:

Ray Flowers: Present
Ray Flower Color: Yellow
Disk Flower Color: Yellow
Anthocyanin in Stigmas: Present
Pollen Color: Yellow
Pappi: Green
Ray length: 45 mm–1.5 mm shorter than comparison
Ray width: 12.0 mm–2.0 mm narrower than comparison
HEAD AT SEED MATURITY:

Diameter: 15.0 cm–1.0 cm wider than comparison
Receptacle shape: Flat
Head attitude: Descending
Number of seeds per head: 551–101 seeds/head more than comparison
SEEDS:

Outer pericarp: Striped brown
Middle pericarp: White
Inner pericarp (seed coat): No color
Stripes: Narrow white
Mottling: Absent TABLE 1-continued

VARIETY DESCRIPTION INFORMATION

Shape: Narrowly ovate
Shape (cross-section): Curved
Length: 7.9 mm–1.3 mm shorter than comparison
Weight: 2.2 gm/100 seeds - 0.7 gm lighter than comparison
% held on 7.9 mm (10/64) round-hole screen: 0 - Same as comparison
DISEASE, PARASITES AND INSECTS:

Down Mildew (*Plasmopara halstedii*): Susceptible
Sclerotinia Wilt (*Sclerotinia sclerotiorum*): Susceptible
Phoma Black Stem (*Phonma macdonaldii*): Susceptible
Phomopsis (*Phomopsis helianthi* = *Diaporthe helianthi*): Susceptible
Sunflower Moth (*Homoeosoma electellum*): Susceptible
Banded Sunflower Moth (*Cochylis hospes*): Susceptible
Seed Weevil (*Smicronyx fulvus* or *S. Sordidus*): Susceptible
Sunflower Midge (*Contarinia schulzi*): Susceptible
Sunflower Beetle (*Zygogramma exclamationis*): Susceptible This invention is also directed to methods for producing a sunflower plant by crossing a first parent sunflower plant with a second parent sunflower plant, wherein the first or second sunflower plant is the inbred sunflower plant from the line H1063R. Further, both first and second parent sunflower plants may be from the inbred line H1063R. Therefore, any methods using the inbred sunflower line H1063R are part of this invention: selfing, backcrosses, hybrid breeding, and crosses to populations. Any plants produced using inbred sunflower line H1063R as a parent are within the scope of this invention. Advantageously, the inbred sunflower line is used in crosses with other sunflower varieties to produce first generation ($F_1$) sunflower hybrid seed and plants with superior characteristics.

H1063R is similar to RHA345, however, there are numerous differences including the plant height. H1063R is shorter in plant height than RHA345.

H1063R is an excellent parent in commercial sunflower hybrids. H1063R has seed with 52–55% oil content. The fatty acid composition of the oil is 89–91% oleic acid with 6.5–6.9 total saturated fatty acids.

Some of the criteria used to select plants in various generations include: seed yield, maturity, plant height, uniformity of plant type, disease and insect resistance, and large seed size. During the development of the line, crosses were made to inbred testers for the purpose of estimating the line's general and specific combining ability. The inbred was evaluated further as a line and in numerous combinations across the Sunflower Belt. The inbred has proven to have a very good combining ability in hybrid combinations.

The inbred has shown uniformity and stability within the limits of environmental influence for all of the traits. The inbred has been self-pollinated and a sufficient number of generations, with careful attention to uniformity of plant type to ensure homozygosity and phenotypic stability necessary to use in commercial production. The line has been increased both by hand and sibbed in isolated fields with continued observations for uniformity. No variant traits have been observed or are expected in H1063R.

FURTHER EMBODIMENTS OF THE INVENTION

This invention also is directed to methods for producing a sunflower plant by crossing a first parent sunflower plant with a second parent sunflower plant wherein either the first or second parent sunflower plant is an inbred sunflower plant of the line H1063R. Further, both first and second parent sunflower plants can come from the inbred sunflower line H1063R. Still further, this invention also is directed to methods for producing an inbred sunflower line H1063R-derived sunflower plant by crossing inbred sunflower line H1063R with a second sunflower plant and growing the progeny seed, and repeating the crossing and growing steps with the inbred sunflower line H1063R-derived plant from 0 to 7 times. Thus, any such methods using the inbred sunflower line H1063R are part of this invention: selfing, backcrosses, hybrid production, crosses to populations, and the like. All plants produced using inbred sunflower line H1063R as a parent are within the scope of this invention, including plants derived from inbred sunflower line H1063R. Advantageously, the inbred sunflower line is used in crosses with other, different, sunflower inbreds to produce first generation ($F_1$) sunflower hybrid seeds and plants with superior characteristics.

It should be understood that the inbred can, through routine manipulation of cytoplasmic or other factors, be produced in a male-sterile form. Such embodiments are also contemplated within the scope of the present claims. The foregoing was set forth by way of example and is not intended to limit the scope of this invention.

As used herein, the term plant includes plant cells, plant protoplasts, plant cell tissue cultures from which sunflower plants can be regenerated, plant calli, plant clumps and plant cells that are intact in plants or parts of plants, such as embryos, pollen, ovules, leaves, stems, cortex, pith, involucral bracts, ray flowers, disk flowers, pappi, achenes, nectaries, interfloral bracts, receptacle, trichomes stigma, anther, style, filament, calyx, pericarp, seed coat, endosperm, embryo, roots, root tips, seeds and the like.

The first reference of plant regeneration from sunflower callus was by Sadhu 1974. "Affective different auxin on growth and differentiation in callus tissue from sunflower stem pith". M. D. & J. Exp. Biol. 12:110–111 (1974). Sadhu isolated stem pithum and eventually regenerated plantlets from a single piece of callus. Standard tissue culture variables such as methods of staging and preparation of explants, composition of culture media, cultural conditions, timing of the regeneration process, plant establishment, and maintenance of fertility have all been delineated for sunflower. Explant sources have included seedling hypocotyl, mature cotyledon, immature cotyledon, immature embryo-somatic embryogenesis, immature embryo-rescued, primary leaflets, meristem, embryonic axis, half apex, unfertilized ovary or ovule, anther, shoot-tip protoplasts, hypocotyl protoplasts, hypocotyl and cotyledon protoplasts. The most favored explants for culture initiation and plant regeneration are mature cotyledons, immature embryos, hypocotyls and excised meristems. For detailed description of culture systems for Helianthus annuus please see Chapter 11, Sunflower Biotechnology, Bidney, D. L. and Scelonge, C. J., pp. 559–593 and references cited therein. Sunflower Technology and Production, edited by A. A. Schneiter, Agronomy 35, publishers, American Society of Agronomy Inc. 1997.

Transformation of Sunflower

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transgenic versions of the claimed inbred sunflower line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed sunflower plants, using transformation methods as described below to incorporate transgenes into the genetic material of the sunflower plant(s).

Expression Vectors for Sunflower Transformation Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (npfII) gene, isolated from transposon Tn5, which when placed under the control of plant regulatory signals which confers resistance to kanamycin. Fraley et al., *Proc. Natl. Acad. Sci. U.S.A.*, 80:4803 (1983). Another commonly used selectable marker gene is the hybrimycin phosphotransferase gene which confers resistance to the antibiotic hybrimycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990< Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984). Another approach to the identification of relatively rare transformation events has been use of a gene that encodes a dominant constitutive regulator of the *Zea mays* anthocyanin pigmentation pathway. Ludwig et al., *Science* 247:449 (1990).

Recently, in vivo methods for visualizing GUS activity that do not require destruction of plant tissue have been made available. Molecular Probes publication 2908, Imagene Green™, p. 1–4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in sunflower. Optionally, the inducible promoter is operably linked to a nucleotide sequence encoding a signal sequence which is operably linked to a gene for expression in sunflower. With an inducible promoter the rate of transcription increases in response to an inducing agent.

Any inducible promoter can be used in the instant invention. See Ward et al., *Plant Mol. Biol.* 22:361–366 (1993). Exemplary inducible promoters include, but are not limited to, that from the ACEI system which responds to copper (Meft et al., *PNAS* 90:4567–4571 (1993)); In2 gene from maize which responds to benzenesulfonamide herbicide safeners (Hershey et al., *Mol. Gen Genetics* 227:229–237

(1991) and Gatz et al., *Mol. Gen. Genetics* 243:32–38 (1994)) or Tet repressor from Tn10 (Gatz et al., *Mol. Gen. Genetics* 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in sunflower or the constitutive promoter is operably linked to a nucleotide sequence encoding a signal sequence which is operably linked to a gene for expression in sunflower.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-Specific or Tissue-Preferred Promoters

A tissue-specific promoter is operably linked to a gene for expression in sunflower. Optionally, the tissue-specific promoter is operably linked to a nucleotide sequence encoding a signal sequence which is operably linked to a gene for expression in sunflower. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476–482 (1983) and Sengupta-Gopalan et al., *Proc. Natl. Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217:240–245 (1989)); a pollen-specific promoter such as that from Zm13 (Guerrero et al., *Mol. Gen. Genetics* 244:161–168 (1993)) or a microspore-preferred promoter such as that from apg (Twell et al., *Sex. Plant Reprod.* 6:217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3–17 (1987), Lerner et al., *Plant Physiol.* 91:124–129 (1989), Fontes et al., *Plant Cell* 3:483–496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is sunflower. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology *CRC Press, Boca Raton* 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains. See, for example Jones et al., *Science* 266:789 (1994) (cloning of the tomato Cf-9 gene for resistance to

*Cladosporium fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo α-1, 4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A development-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes That Confer Resistance to a Herbicide:

A. A herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy propionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. A herbicide that inhibits photosynthesis, such as a triazine (psbA and gs+genes) and a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes That Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased Phytate Content

1) Introduction of a phytase-encoding gene would enhance breakdown of phytate, adding more free phosphate to the transformed plant. For example, see Van Hartingsveldt et al., *Gene* 127:87 (1993); for a disclosure of the nucleotide sequence of an *Aspergillus niger* phytase gene.

2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

Methods for Sunflower Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89–119.

A. *Agrobacterium*-Mediated Transformation

One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997. The first sunfloweor transformations with engineered strains of *Agrobacterium* were reported in 1983 in which Phaseolin was inserted into T-DNA of the Ti plasmid and inoculated to sunflower seedlings. Murai et al. (1983) "Phaseolin Gene From Bran is Expressed After Transfer to Sunflower", Science, 222:475–482. Sunflower is susceptible to *Agrobacterium* infection and it remains the most efficient and popular transformation protocol. Knittel et al., "Transformation of Sunflower/*Helianthus annuus* L.) A Retrievable Protocol", Plant Cell Rep. 14:81–86; Malone-Schoneberg, J., et al. 1994, "Stable Transformation of Sunflower Using *Agrobacterium* and Split Embryonic Axis Explants", Plant Science, 103:119–207.

B. Direct Gene Transfer

Despite the fact the host range for *Agrobacterium*-mediated transformation is broad, some major cereal crop species and gymnosperms have generally been recalcitrant to this mode of gene transfer, even though some success has recently been achieved in rice and sunflower. Hiei et al., *The Plant Journal* 6:271–282 (1994) and U.S. Pat. No. 5,591, 616 issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992). In sunflower, several target tissues can be bombarded with DNA-coated microprojectiles in order to produce transgenic plants, including, for example, callus (Type I or Type II), immature embryos, and meristematic tissue. Several target tissues can be bombarded with DNA-coated microprojectiles in order to produce transgenic plants, including, for example, callus (Type I or Type II), immature embryos, and meristematic tissue. In sunflower microprojectile bombardment efficiency is low. Experiments with sunflower meristems designed to compare stable transformation efficiency of microprojectile bombardment to deliver plasmid DNA with bombardment used only to induce wounds to facilitate *Agrobacterium* transformation showed the frequency of positive transformants nearly 300 fold higher in the latter protocol. Bidney et al., "Microprojectile Bombardment of Plant Tissues Increases Transformation Frequency by *Agrobacterium* tumefaciens", Plant Mol. Biol. 18:301–313 (1993).

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-omithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of Vllth International Congress on Plant Cell and Tissue Culture IAPTC, A2-38, p 53 (1990); D'Halluin et al., *Plant Cell* 4:1495–1505 (1992) and Spencer et al., *Plant Mol. Biol.* 24:51–61 (1994).

Following transformation of sunflower target tissues, expression of the above-described selectable marker genes allows for preferential selection of transformed cells, tissues and/or plants, using regeneration and selection methods now well known in the art.

Several sunflower transformant protocols have evolved which allow for the identification of transformants without the need for selectable markers. Nutler et al. 1987, "Factors Affecting the Level of Kanamycin Resistance in Transformed Sunflower Cells", Plant Physiol. 84:1185–1192. See also, Bidney, D., et al., supra, using intact meristem explants and analyzing gene in leaf tissue via protein methods such as ELISA or enzyme assay or nucleic acid methods such as PCR or RT-PCTR.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular sunflower line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

INDUSTRIAL APPLICABILITY

Sunflower (*Helianthus annuus*) oil is a major edible oil worldwide. The oil component of sunflower seeds typically contributes about 80% of the value of a sunflower crop and is mostly used as a cooking medium. Sunflower oil is also used as salad oil, as well as in the manufacture of margarine, soap, shortening, lubricants, and as a source for biodiesel fuels. In the United States, approximately 1–2 million acres are planted in sunflowers annually, primarily in the Dakotas and Minnesota.

The seed of inbred sunflower line H1063R, the plant produced from the inbred seed, the hybrid sunflower plant produced from the crossing of the inbred, hybrid seed, and various parts of the hybrid sunflower plant can be utilized for human food, livestock feed, and as a raw material in industry.

When the term inbred sunflower plant is used in the context of the present invention, this also includes any single gene conversions of that inbred. The term single gene converted plant as used herein refers to those sunflower plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental sunflower plants for that inbred. The parental sunflower plant which contributes the gene for the desired characteristic is termed the nonrecurrent or donor parent. This terminology refers to the fact that the nonrecurrent parent is used one time in the backcross protocol and therefore does not recur. The parental sunflower plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a sunflower plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, herbicide resistance, resistance for bacterial, fungal, or viral disease, insect resistance, male fertility, enhanced nutritional quality, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

TABLES

In the table that follows, the traits and characteristics of inbred sunflower line H1063R are given in hybrid combination. The data collected on inbred sunflower line H1063R is presented for the key characteristics and traits. The table presents yield test information about H1063R. H1063R was tested in several hybrid combinations at numerous locations, with two or three replications per location. Information about these hybrids, as compared to several check hybrids, is presented.

The first pedigree listed in the comparison group is the hybrid containing H1063R. The following symbols in Tables 1–6, +, *, **, denote significance at the 0.10, 0.05, and 0.01 levels of probability, respectively.

oleic commercial hybrids. This data demonstrates the yield potential H1063R contributes in hybrid combinations.

TABLE 1

Head to Head Comparison in Hybrid Combination

| Years | Locs | Pedigree | FLR | HT | TW | MST | YLD | OLE | OIL |
|---|---|---|---|---|---|---|---|---|---|
| 00–01 | 11 | X80454 | 77 | 63 | 29.2 | 11.4 | 2541 | 66.5 | 44.0 |
|  |  | 8377NS | 75** | 69** | 27.9** | 10.8** | 2414* | 63.1 | 43.0 |
| 00–01 | 11 | X80454 | 72 | 63 | 29.5 | 11.3 | 2524 | 66.5 | 44.4 |
|  |  | Cavalry | 73 | 78** | 30.0** | 10.6** | 2413* | 21.8** | 46.7** |
| 99–01 | 15 | X80454 | 68 | 64 | 29.4 | 11.4 | 2345 | 63.0 | 44.4 |
|  |  | SF290 | 67 | 64 | 27.8** | 11.1 | 2366 | 53.0 | 41.4** |

X80454 is a NuSun hybrid having H1063R as the male parent. NuSun hybrids have "mid-oleic" oil, from 55–<80% oleic. These are made by several methods including crossing a high oleic inbred with a normal or linoleic inbred, blending high oleic and inoleic hybrid seed from related or unrelated crosses, crossing inbred parents segregating for high oleic, and crossing mid-oleic inbreds. Other methods are possible.

TABLE 2

Head to Head Comparison in Hybrid Combination

| Years | Locs | Pedigree | FLR | HT | TW | MST | YLD | OLE | OIL |
|---|---|---|---|---|---|---|---|---|---|
| 00 | 7 | X80423 | 77 | 67 | 28.2 | 11.4 | 2603 | 86.6 | 42.1 |
|  |  | 7330 | 75* | 70+ | 27.2 | 9.4** | 2352** | 87.3 | 42.2 |
| 00 | 5 | X80423 | 77 | 70 | 28.3 | 11.2 | 2406 | 87.4 | 43.3 |
|  |  | 858 | 76 | 70 | 26.6** | 9.6** | 2086** | 83.9 | 45.0 |
| 00–01 | 12 | X80423 | 77 | 65 | 28.6 | 11.5 | 2498 |  | 42.7 |
|  |  | Cavalry | 77 | 76** | 29.0* | 9.9** | 2470 |  | 46.6** |
| 01 | 6 | X80423 | 76 | 65 | 29.1 | 11.0 | 2047 | 88.4 | 40.2 |
|  |  | P63M80 | 74 | 71 | 29.2 | 10.4 | 1923 | 73.0 | 42.7* |

X80423 is a high oleic hybrid using H1063R as the male parent. 7330 and 858 are Mycogen Seeds' proprietary high

TABLE 3

Head to Head Comparison in Hybrid Combination

| Years | Locs | Pedigree | FLR | HT | TW | MST | YLD | OLE | OIL |
|---|---|---|---|---|---|---|---|---|---|
| 99–01 | 12 | X80357 | 71 | 66 | 28.4 | 10.2 | 2469 | 73.9 | 43.5 |
|  |  | 8372 | 70* | 68 | 29.3** | 9.8* | 2439 | 26.7** | 44.5+ |
| 99–01 | 11 | X80357 | 70 | 68 | 28.5 | 10.5 | 2317 | 73.9 | 453 |
|  |  | SF290 | 71** | 64* | 27.8** | 11.1** | 2274 | 46.9 | 41.6** |
| 99–01 | 11 | X80357 | 71 | 67 | 28.5 | 10.5 | 2446 | 73.9 | 45.3 |
|  |  | SF270 | 69** | 67 | 29.2** | 10.0** | 2442 | 35.9** | 41.9** |

X80357 is a NuSun hybrid that uses H1063R as the male parent. 8372 is a leading normal or linoleic hybrid commercially in its maturity. The male of 8372 is closely related to H1063R, but is linoleic. This comparison demonstrates the yield potential and oleic contributions of H1063R to produce elite commercially competitive hybrids.

TABLE 4

Head to Head Comparison in Hybrid Combination

| Years | Locs | Pedigree | FLR | HT | TW | MST | YLD | OLE | OIL |
|---|---|---|---|---|---|---|---|---|---|
| 99–01 | 12 | E81458 | 71 | 72 | 29.1 | 10.3 | 2318 | 65.4 | 44.1 |
|  |  | 8377NS | 70 | 73 | 28.1* | 10.3 | 2187* | 63.1 | 43.3 |
| 99–01 | 12 | E81458 | 74 | 73 | 29.2 | 10.3 | 2309 | 65.3 | 44.1 |
|  |  | Cavalry | 76** | 80** | 29.6 | 10.6 | 2329 | 23.6** | 46.2* |
| 00–01 | 8 | E81458 | 70 | 72 | 30.1 | 10.1 | 2157 | 64.7 | 44.4 |
|  |  | SF290 | 70 | 67* | 28.2* | 11.6** | 1984* | 53.5 | 40.8** |
| 01 | 4 | E81458 | 73 | 70 | 29.0 | 10.0 | 2190 |  | 44.6 |
|  |  | SF187 | 73 | 66 | 28.6 | 9.9 | 2230 |  | 40.8** |

E81358 is a NuSun hybrid using H1063R. Again, the data demonstrates the yield potential of H1063R in hybrid combinations as well as good oil levels and oleic content.

TABLE 5

Head to Head Comparison in Hybrid Combination

| Years | Locs | Pedigree | FLR | HT | TW | MST | YLD | OLE | OIL |
|---|---|---|---|---|---|---|---|---|---|
| 99 | 4 | X80321 | 67 | 76 | 30.2 | 11.1 | 2199 | 85.9 | 41.6 |
|  |  | 8377NS | 66 | 73 | 29.1 | 10.7 | 2148 | 60.4** | 44.6** |
| 00 | 6 | X80321 | 74 | 68 | 27.4 | 9.5 | 2589 | 90.1 | 43.5 |
|  |  | 7330 | 74 | 70 | 27.2 | 9.1** | 2351** | 88.5 | 42.2 |
| 99 | 2 | X80321 | 67 | 70 | 30.1 | 11.9 | 1817 | 85.9 | 42.8 |
|  |  | SF270 | 66+ | 71 | 27.9* | 9.8** | 2158** | 31.1** | 40.5* |
| 01 | 4 | X80321 | 70 | 66 | 28.6 | 11.0 | 2530 | 88.7 | 45.0 |
|  |  | SF270 | 69** | 64 | 30.3** | 10.8 | 2311+ | Na | 42.5 |

X80321 is the hybrid pre-commercial number that will be sold commercially as 7350.

TABLE 6

Head to Head Comparison in Hybrid Combination

| Years | Locs | Pedigree | FLR | HT | TW | MST | YLD | OLE | OIL |
|---|---|---|---|---|---|---|---|---|---|
| 99–01 | 5 | X80321 | 66 | 73 | 29.6 | 10.5 | 2431 | 88.3 | 43.0 |
|  |  | Pioneer 63A51 | 66 | 73 | 30.7* | 10.1+ | 2296 | 87.9 | 40.9 |

Table 6 shows the improved yield, oil and oleic levels of X80321 as compared to the Pioneer high oleic hybrid 63A51.

TABLE 7

Fatty Acid Comparison of Three High Oleic Hybrids

| Hybrid | Oleic % | TOTSAT % |
|---|---|---|

| | | |
|---|---|---|
| X80321 (Female A × H1063R) | 88.3 | 7.20 |
| 7330 (Female A × Male B) | 87.1 | 8.36 |
| Pioneer 63A51 | 87.9 | 8.35 |

Data Averages from Prescott, Wis. and Breckenridge, Minn. in 2001.

Table 7 shows that X80321 and 7330 use the same high oleic female. Also shown is the effect of H1063R to increase oleic content and lower levels of saturated fatty acids significantly. Additionally, it is shown that X80321 is unique in having lowered saturates compared to two leading commercial high oleic hybrids.

TABLE 8

Single Seed Analysis

| Sample ID | Oleic - C18:1 | TOTSAT % |
|---|---|---|
| H1063R | 90.44 | 6.80 |
| H1063R | 90.91 | 6.58 |
| 6008446-2 | 88.60 | 8.70 |
| 6008446-11 | 88.99 | 8.77 |
| 6009643-9 | 87.02 | 10.38 |
| 6009643-11 | 88.40 | 9.31 |

This data shows that H1063R has very high oleic levels and much lower total saturates compared to other elite lines.

DEPOSIT INFORMATION

A deposit of the inbred sunflower line of this invention is maintained by Agrigenetics, Inc. d/b/a Mycogen Seeds, Highway 75 North, Breckenridge, Minn. 56520. Access to this deposit will be available during the pendency of this application to persons determined by the Commissioner of Patents and Trademarks to be entitled thereto under 37 CFR 1.14 and 35 USC 122. Upon allowance of any claims in this application, all restrictions on the availability to the public of the variety will be irrevocably removed by affording access to a deposit of at least 2,500 seeds of the same variety with the American Type Culture Collection, Manassas, Va.

Although the foregoing invention has been described in some detail by way of illustration and example for purposes of clarity and understanding. However, it will be obvious that certain changes and modifications such as single gene modifications and mutations, somoclonal variants, variant individuals selected from large populations of the plants of the instant inbred and the like may be practiced within the scope of the invention, as limited only by the scope of the appended claims.

What is claimed is:

1. A seed of sunflower inbred line designated H1063R, representative seed of said line having been deposited under ATCC Accession No. PTA-6657.

2. A sunflower plant, or part thereof, produced by growing the seed of claim 1.

3. Pollen of the plant of claim 2.

4. An ovule of the plant of claim 2.

5. A sunflower plant, or parts thereof, having all of the physiological and morphological characteristics of the sunflower plant of claim 2.

6. A tissue culture of regenerable cells from the sunflower plant of claim 2.

7. The tissue culture according to claim 6, wherein a cell or protoplast of the tissue culture is derived from a plant part selected from the group consisting of leaves, pollen, embryos, roots, root tips, anthers, flowers, and stalks.

8. A sunflower plant regenerated from the tissue culture of claim 6, wherein the regenerated plant has all of the morphological and physiological characteristics of inbred line H1063R, representative seed of said line H1063R having been deposited under ATCC Accession No. PTA-6657.

9. A sunflower plant with all of the physiological and morphological characteristics of inbred line H1063R, wherein said sunflower plant is produced by a tissue culture process using the sunflower plant of claim 5 as the starting material for said process.

10. A method for producing a hybrid sunflower seed, wherein said comprises crossing a first inbred parent sunflower plant with a second inbred parent sunflower plant and harvesting the resultant hybrid sunflower seed, wherein said first inbred parent sunflower plant or said second inbred parent sunflower plant is the sunflower plant of claim 2.

11. A method for producing a male-sterile sunflower plant comprising transforming the sunflower plant of claim 2 with a nucleic acid molecule that confers male sterility.

12. A male sterile sunflower plant produced by the method of claim 11.

13. A method of producing an herbicide resistant sunflower plant comprising transforming the sunflower plant of claim 2 with a transgene that confers herbicide resistance.

14. An herbicide resistant sunflower plant produced by the method of claim 13.

15. The sunflower plant of claim 14, wherein the transgene confers resistance to an herbicide selected from the group consisting of imidazolinone, sulfonylurea, glyphosate, glufosinate, L-phosphinothricin, triazine and benzonitrile.

16. A method of producing an insect resistant sunflower plant comprising transforming the sunflower plant of claim 2 with a transgene that confers insect resistance.

17. An insect resistant sunflower plant produced by the method of claim 16.

18. The sunflower plant of claim 17, wherein the transgene encodes a *Bacillus thuringiensis* endotoxin.

19. A method of producing a disease resistant sunflower plant comprising transforming the sunflower plant of claim 2 with a transgene that confers disease resistance.

20. A disease resistant sunflower plant produced by the method of claim 19.

21. A method of introducing a desired trait into sunflower inbred line H1063R, wherein the method comprises:
 (a) crossing H1063R plants grown from H1063R seed, representative seed of which has been deposited under ATCC Accession No. PTA-6657, with plants of another sunflower line that comprise a desired trait to produce progeny plants, wherein the desired trait is selected from the group consisting of male sterility, herbicide resistance, insect resistance, disease resistance and oil content;
 (b) selecting progeny plants that have the desired trait to produce selected progeny plants;
 (c) crossing the selected progeny plants with the H1063R plants to produce backcross progeny plants;
 (d) selecting for backcross progeny plants that have the desired trait and physiological and morphological characteristics of sunflower inbred line H1063R to produce selected backcross progeny plants; and
 (e) regeating steps (c) and (d) three more times in succession to produce selected fourth or higher backcross progeny plants that comprise the desired trait and all of the physiological and morphological characteristics of sunflower inbred line H1063R listed in Table 1.

22. A plant produced by the method of claim 21, wherein the plant has the desired trait and all of the physiological and morphological characteristics of sunflower inbred line H1063R listed in Table 1.

23. The plant of claim 22, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

24. The plant of claim 22 wherein the desired trait is insect resistance and the insect resistance is conferred by a transgene encoding a *Bacillus thuringiensis* endotoxin.

25. The plant of claim 22 wherein the desired trait is male sterility and the trait is conferred by a cytoplasmic nucleic acid molecule that confers male sterility.

* * * * *